US012808883B2

(12) United States Patent
Huschto et al.

(10) Patent No.: US 12,808,883 B2
(45) Date of Patent: Nov. 24, 2026

(54) METHOD FOR SCREENING A SUBJECT FOR THE RISK OF CHRONIC KIDNEY DISEASE

(71) Applicant: Roche Diabetes Care, Inc., Indianapolis, IN (US)

(72) Inventors: Tony Huschto, Speyer (DE); Helena Koenig, Griesheim (DE); Christian Ringemann, Mannheim (DE)

(73) Assignee: Roche Diabetes Care, Inc, Indianapolis, IN (US)

( * ) Notice: Subject to any disclaimer, the term of this patent is extended or adjusted under 35 U.S.C. 154(b) by 695 days.

(21) Appl. No.: 18/467,043

(22) Filed: Sep. 14, 2023

(65) Prior Publication Data

US 2023/0417772 A1 Dec. 28, 2023

Related U.S. Application Data

(63) Continuation of application No. PCT/EP2022/056707, filed on Mar. 15, 2022.

(30) Foreign Application Priority Data

Mar. 15, 2021 (EP) .................................... 21162683

(51) Int. Cl.
*G16H 50/30* (2018.01)
*G01N 33/68* (2006.01)

(52) U.S. Cl.
CPC ......... *G01N 33/6893* (2013.01); *G16H 50/30* (2018.01); *G01N 2800/347* (2013.01)

(58) Field of Classification Search
None
See application file for complete search history.

(56) References Cited

U.S. PATENT DOCUMENTS

2020/0005900 A1 1/2020 Cha et al.

FOREIGN PATENT DOCUMENTS

EP 3 543 702 A 9/2019
WO WO-2015140551 A1 * 9/2015 ............. G16H 50/30
WO WO-2019180232 A1 * 9/2019 ......... G01N 33/6893

OTHER PUBLICATIONS

Hosseinzadeh Mehdi et al: "A diagnostic prediction model for chronic kidney disease in internet of things platform," Multimedia Tools and Applications, US, vol. 80, No. 11, Jul. 29, 2020 (Jul. 29, 2020), pp. 16933-16950, XP037458777.*

(Continued)

*Primary Examiner* — Yung-Sheng M Tsui
(74) *Attorney, Agent, or Firm* — Bose McKinney & Evans LLP

(57) ABSTRACT

A method for screening a subject for the risk of chronic kidney disease (CKD) is provided. Marker data indicative for a plurality of marker parameters for a subject is received. The marker parameters indicate at least an age value, a time since diagnosis value indicative of a time since a diabetes diagnosis for the subject, a sample level of creatinine, an estimated glomerular filtration rate, a sample level of albumin, and a sample level of blood urea nitrogen. A risk factor is determined that indicates the risk of suffering CKD for the subject from the plurality of marker parameters.

13 Claims, 3 Drawing Sheets

(56) References Cited

OTHER PUBLICATIONS

Piscitelli et al, Predictors of chronic kidney disease in type 1 diabetes: a longitudinal study from the AMD Annals initiative, Sci Rep. Jun. 12, 2017;7:3313. doi: 10.1038/s41598-017-03551-w.*
International Search Report and Written Opinion of the International Searching Authority, PCT/EP2022/056707, Jun. 27, 2022, 12 pages.
Liu et al., Investigation of the Prevalence of CKD in 13,383 Chinese Hospitalized Adult Patients, Clinica Chimica Acta, vol. 387, 2007, No. 1, pp. 128-132.
Lu et al., High Prevalence of Chronic Kidney Disease in Population-Based Patients Diagnosed with Type 2 Diabetes in Downtown Shanghai, Journal of Diabetes and its Complications, Elsevier Science, 2008, vol. 22, No. 2, pp. 96-103.
Zhang et al., Biomarkers of Renal Function in Type 2 Diabetic Patients with Cognitive Impairment, Neuroscience Letters, 2016, vol. 610, pp. 19-23.
Huschto et al., 476-P: Predicting the Risk of Chronic Kidney Disease in People with Diabetes (PWD) from Electronic Health Care Records (EHRs): A Validation Study, Diabetes, 2020, vol. 69, Supplement 1, 476-P, 4 pages.
Afshar et al., 15-LB: Prediction of Chronic Kidney Disease (CKD) in People with Diabetes, Diabetes, 2021, vol. 70, Supplement 1, 15-LB, 4 pages.
Hosseinzadeh et al., A Diagnostic Prediction Model for Chronic Kidney Disease in Internet of Things Platform, Multimedia Tools and Applications, 2020, vol. 80, No. 11, pp. 16933-16950.
Glassock et al., The Global Burden of Chronic Kidney Disease: Estimates, Variability and Pitfalls, Nature Reviews Nephrology, 2017, vol. 113, No. 2, pp. 104-114.
Platinga et al., Awareness of Chronic Kidney Disease among Patients and Providers, Advances in Chronic Kidney Disease, 2010, vol. 17, No. 3, pp. 225-236.
Fioretto et al., Residual Microvascular Risk in Diabetes: Unmet Needs and Future Directions, Nature Reviews Endocrinology, 2010, Vo. 6, No. 1, pp. 19-25.
Dunkler et al., Risk Prediction for Early CKD in Type 2 Diabetes, Clinical Journal of the American Society of Nephrology, 2015, vol. 10, No. 8, pp. 1371-1379.
Vergouwe et al., Progression to Microalbuminuria in Type 1 Diabetes: Development and Validation of a Prediction Rule, 2010, Diabetologia, vol. 53, pp. 254-262.
Keane et al., Risk Scores for Predicting Outcomes in Patients with Type 2 Diabetes and Nephropathy: The Renaal Study, Clinical Journal of the American Society of Nephrology, 2006, vol. 1, No. 4, pp. 761-767.
Jardine et al., Prediction of Kidney-Related Outcomes in Patients with Type 2 Diabetes., American Journal of Kidney Diseases, 2012, vol. 60, No. 5, pp. 770-778.
Song et al., Longitudinal Risk Prediction of Chronic Kidney Disease in Diabetic Patients Using a Temporal-Enhanced Gradient Boosting Machine: Retrospective Cohort Study, JMIR Medical Informatics, 2020, vol. 8, No. 1, e15510, 16 pages.
Kaelber et al., Patient Characteristics Associated with Venous Thromboembolic Events: A Cohort Study Using Pooled Electronic Health Record Data, Journal of the American Medical Informatics Association, 2012, vol. 19, No. 6, pp. 965-972.
Mcdonald et al., The Indiana Network for Patient Care: A Working Local Health Information Infrastructure, Health Affairs, 2005, vol. 24, No. 5, pp. 1214-1220.
Swets, Measuring the Accuracy of Diagnostic Systems, Science, 1988, vol. 240, No. 4857, pp. 1285-1293.
Bradley, The Use of the Area Under the ROC Curve in the Evaluation of Machine Learning Algorithms, Pattern Recognition, 1997, vol. 30, No. 7, pp. 1145-1159.
Unger et al., Diabetes Management in Primary Care, 2nd Edition. Lippincott Williams & Wilkens, 2013, Philadelphia, USA.
Ogunleye et al., XGBoost Model for Chronic Kidney Disease Diagnosis, IEEE/ACM Transactions on Computational Biology and Bioinformatics, 2020, vol. 17, No. 6, pp. 2131-2140.
Mcfarlane et al., Chronic Kidney Disease in Diabetes, Canadian Journal of Diabetes, 2018, vol. 42, pp. S201-S209.
Praditpornsilpa et al., The need for robust validation for MDRD-based glomerular filtration rate estimation in various CKD populations, Nephrology Dialysis Transplantation, 2011, 6 pages.
Wang et al., Predicting the Risk of Chronic Kidney Disease (CKD) Using Machine Learning Algorithm, Applied Sciences, 2011, pp. 1-17.
Xiao et al., Comparison and development of machine learning tools in the prediction of chronic kidney disease progression, Journal of Translational Medicine, 2019, 17:119, pp. 1-13.
Unger et al., Diabetes Management in Primary Care, 2nd Edition. Lippincott Williams & Wilkens, 2013, Philadelphia, USA, 2013, 21 pages.

* cited by examiner

METHOD FOR SCREENING A SUBJECT FOR THE RISK OF CHRONIC KIDNEY DISEASE

RELATED APPLICATIONS

This application is a continuation of International Application Serial No. PCT/EP2022/056707, filed Mar. 15, 2022, which claims priority to EP 21 162 683.3, filed Mar. 15, 2021, the entire disclosures of both of which are hereby incorporated herein by reference.

BACKGROUND

This disclosure refers to a method for screening a subject for the risk of chronic kidney disease, a computer-implemented method, a system, and a computer program product.

In chronic kidney disease (CKD), kidney function is progressively lost, beginning with a decline in the glomerular filtration rate and/or albuminuria and progressing to end-stage renal disease. As a result, dialysis or renal transplant may be necessary (see Unger, J., Schwartz, Z., *Diabetes Management in Primary Care,* 2nd edition. Lippincott Williams & Wilkens, Philadelphia, USA, 2013). CKD is a serious problem, with an adjusted prevalence of 7% in 2013 (Glassock, R. J. et al., *The global burden of chronic kidney disease: estimates, variability and pitfalls*, Nat Rev Nephrol 13, 104-114, 2017). The early recognition of CKD could slow progression, prevent complications, and reduce cardiovascular-related outcomes (Platinga, L. C. et al., *Awareness of chronic kidney disease among patients and providers*, Adv Chronic Kidney Dis 17, 225-236, 2010). CKD may be a microvascular long-term complication of diabetes (Fioretto, P. et al., *Residual microvascular risk in diabetes: unmet needs and future directions*, Nat Rev Endocrinol 6, 19-25, 2010).

Algorithms for risk prediction of CKD by diabetic patients have been published, for example, by Dunkler et al. (Dunkler, D. et al., *Risk Prediction for Early CKD in Type 2 Diabetes*, Clin J Am Soc Nephrol 10, 1371-1379, 2015), Vergouwe et al. (Vergouwe, Y. et al., *Progression to microalbuminuria in type 1 diabetes: development and validation of a prediction rule*, Diabetologia 53, 254-262, 2010), Keane et al. (Keane, W. F. et al., *Risk Scores for Predicting Outcomes in Patients with Type 2 Diabetes and Nephropathy: The RENAAL Study*, Clin J Am Soc Nephrol 1, 761-767, 2006) and Jardine et al (Jardine, M. J. et al., *Prediction of Kidney-Related Outcomes in Patients With Type 2 Diabetes*, Am J Kidney Dis. 60, 770-778, 2012). Such published algorithms are derived from data originating from major clinical studies.

Such predictive models based on clinical data represent an ideal setting with a preselected population, cross-checked and validated clinical data entries and often a narrow time window of observation. The outcomes therefore do not necessarily reveal the optimum pathways in terms of efficacy and effectiveness for a real-world population when inferred from clinical studies. In addition, most literature is focused on progression of diabetic nephropathy or CKD and therefore misses the early phase of this diabetic complication. Finally, patients are usually selected on the basis of a full set of respective features.

EP 3 543 702 A1 discloses a method for screening a subject for the risk of chronic kidney disease, disclosing receiving marker data indicative for a plurality of marker parameters for a subject, such plurality of marker parameters indicating, for the subject for a measurement period, an age value, a sample level of creatinine, and a sample level of albumin; and determining a risk factor indicative of the risk of suffering CKD for the subject from the plurality of marker parameters. The determining comprises weighting the age value higher than the sample level of albumin, and weighting the sample level of creatinine higher than the sample level of albumin. A computer-implemented method is disclosed applying a logistic regression (LR) model for determining the risk of chronic kidney disease for a subject, such as a patient having received a diabetes diagnose.

A method for longitudinal risk prediction of CKD in diabetic patients has been published by Song et al. (Song et al., *Longitudinal risk prediction of chronic kidney disease in diabetic patients using a temporal-enhanced gradient boosting machine: retrospective cohort study*, JMIR Med Inform 8(1), 2020, e15510). For predicting the risk of CKD a boosted machine learning model is proposed.

SUMMARY

This disclosure provides an improved method for screening a subject for the risk of chronic kidney disease, allowing a reliable risk assessment for CKD based on real world data (RWD).

According to an aspect, a method for screening a subject for the risk of chronic kidney disease (CKD) is provided, comprising receiving marker data indicative for a plurality of marker parameters for a subject, such plurality of marker parameters indicating at least the following: an age value, a time since diagnosis value indicative of a time since a diabetes diagnosis for the subject, a sample level of creatinine, an estimated glomerular filtration rate, a sample level of albumin, and a sample level of blood urea nitrogen. A risk factor indicative of the risk of suffering CKD is determined for the subject from the plurality of marker parameters.

According to another aspect, computer-implemented method for screening a subject for the risk of chronic kidney disease (CKD) in a data processing system is provided, the data processing system having a processor and a non-transitory memory storing a program causing the processor to execute: receiving marker data indicative for a plurality of marker parameters for a subject, such plurality of marker parameters indicating an age value, a time since diagnosis value indicative of a time since a diabetes diagnosis for the subject, a sample level of creatinine, a sample level of estimated glomerular filtration rate, a sample level of albumin, and a sample level of blood urea nitrogen; and determining a risk factor indicative of the risk of suffering CKD for the subject from the plurality of marker parameters.

A system is provided, comprising a processor and a non-transitory memory storing a program causing the processor to perform the method for screening a subject for the risk of chronic kidney disease (CKD).

A computer program or a computer program product is provided, comprising instructions which, when the program is executed by a computer, cause the computer to carry out steps of the method for screening a subject for the risk of chronic kidney disease (CKD).

The marker parameters may be indicative of real-world data which is not restricted regarding, for example, completeness or veracity of the data (unlike clinical data).

The time since diagnosis value refers to the time period from the time or date of an initial diabetes diagnosis for the subject to the date of determining the risk factor for the subject.

The method may further comprise the plurality of marker parameters indicating, for the subject, a blood sample level of creatinine. As the sample level of creatinine a serum sample level or a plasma sample may also be used. Thus, requesting the sample level of creatinine as a concentration in urine may be avoided. The plurality of marker parameters may indicate, for the subject, a selected blood sample level (or serum or plasma sample level) of creatinine selected from a plurality of blood sample levels (or serum or plasma sample levels, respectively) of creatinine. For example, the selected blood sample level of creatinine may be a maximum value from the plurality of blood sample levels of creatinine. Alternatively or additionally, the plurality of marker parameters may indicate, for the subject, a calculated blood sample level of creatinine calculated from a plurality of blood sample levels of creatinine. For example, the calculated blood sample level of creatinine may be a statistical value calculated from the plurality of blood sample levels of creatinine, such as a mean, median or mode value. The sample level of creatinine may be provided in units of mg/dl (such as milligrams of creatinine per deciliter of blood).

The method may further comprise the plurality of marker parameters indicating, for the subject, at least one of a blood sample level of albumin and a urine sample level of albumin. In one embodiment, the sample level of albumin is a blood sample level. As the sample level of albumin a serum sample level or a plasma sample may also be used. The plurality of marker parameters may also indicate, for the subject, a selected blood sample level (or serum or plasma sample level) of albumin selected from a plurality of blood sample levels (or serum or plasma sample levels, respectively) of albumin. For example, the selected blood sample level of albumin may be a minimum value from the plurality of blood sample levels of albumin. Alternatively or additionally, the plurality of marker parameters may indicate, for the subject, a calculated blood sample level of albumin calculated from a plurality of blood sample levels of albumin. For example, the calculated blood sample level of albumin may be a statistical value calculated from the plurality of blood sample levels of albumin, such as a mean, median or mode value. The sample level of albumin may be provided in units of mg/dl (such as milligrams of albumin per deciliter of blood).

The glomerular filtration rate is known in the art to be indicative of the flow rate of filtered fluid through the kidney. It is an important indicator for estimating renal function. The glomerular filtration rate may decrease due to renal disease. In embodiments, the glomerular filtration rate may be estimated using a Modification of Diet in Renal Disease (MDRD) formula, known in the art as such. For example, a MDRD formula using four variables relies on age, sex, ethnicity and serum creatinine of the subject for estimating glomerular filtration rate. In alternative embodiments, the glomerular filtration rate may be estimated using the CKD-EPI (Chronic Kidney Disease Epidemiology Collaboration) formula, known in the art as such. The CKD-EPI formula relies on age, sex, ethnicity and serum creatinine of the subject for estimating glomerular filtration rate. In further embodiments, the glomerular filtration rate may be estimated using other methods or may be directly determined. The estimated glomerular filtration rate may be provided in units of ml/min/1.73 $m^2$ (milliliters per minute per 1.73 square meters of body surface area).

The plurality of marker parameters may indicate, for the subject, a selected estimated glomerular filtration rate selected from a plurality of estimated glomerular filtration rates. For example, the selected estimated glomerular filtration rate may be a minimum value from the plurality of estimated glomerular filtration rates. Alternatively or additionally, the plurality of marker parameters may indicate, for the subject, a statistical value as the estimated glomerular filtration rated, calculated from a plurality of estimated glomerular filtration rates, such as a mean, median or mode value.

The sample level of blood urea nitrogen (BUN) may be provided in units of mg/dl (such as milligrams of urea nitrogen per deciliter of blood). The sample level of blood urea nitrogen (BUN) may thus represent the mass of nitrogen within urea/volume of the blood sample, not the mass of whole urea. The plurality of marker parameters may indicate, for the subject, a selected sample level of blood urea nitrogen, selected from a plurality of blood sample levels of urea nitrogen. For example, the selected blood sample level of urea nitrogen may be a minimum value from the plurality of blood sample levels of urea nitrogen. Alternatively or additionally, the plurality of marker parameters may indicate, for the subject, a calculated blood sample level of urea nitrogen calculated from a plurality of blood sample levels of urea nitrogen. For example, the calculated blood sample level of urea nitrogen may be a statistical value calculated from the plurality of blood sample levels of urea nitrogen, such as a mean, median or mode value.

The sample level of creatinine, the sample level of albumin, the sample level of blood urea nitrogen and/or the estimated glomerular filtration rate may be a representative sample level and/or rate from the respective plurality of sample levels and/or rates, such as a maximum sample level and/or rate, a minimum sample level and/or rate, a mean sample level and/or rate and or a median of the sample levels and/or rates, respectively. In an exemplary embodiment, creatinine is a maximum sample level of creatinine from a plurality of sample levels of creatinine for the subject, albumin is a minimum sample level of albumin from a plurality of sample levels of albumin for the subject, eGFR is a minimum estimated glomerular filtration rate from a plurality of estimated glomerular filtration rates for the subject and blood urea nitrogen is a minimum sample level of blood urea nitrogen from a plurality of sample levels of blood urea nitrogen for the subject.

The marker data may stem from a measurement period of two years or less. The measurement period may thus be limited to two years. Thereby, values and/or sample levels of sub-stances may be provided that have been collected within a time period of a maximum of two years with the risk factor indicating a risk of suffering CKD for the subject from the end of the measurement period onwards.

In one embodiment, at least the sample level of creatinine, the sample level of albumin, the sample level of blood urea nitrogen, and the estimated glomerular filtration rate stem from a measurement period of two years or less. The samples for determining the sample level of creatinine, the sample level of albumin, the sample level of blood urea nitrogen, and estimated glomerular filtration rate may have been taken and/or determined in a measurement period of two years or less.

The age value may correspond to the age of the patient (e.g., in years) when determining the risk factor.

The time since diagnosis value may be indicative of the time since a diabetes diagnosis for the subject when determining the risk factor. In one embodiment, the date of determining the risk factor for the subject may be defined as the end of the measurement period.

The risk factor indicative of the risk of suffering CKD for the subject is determined from the plurality of marker parameters, including at least the age value of the subject, the time since diagnosis value indicative of the time since the diabetes diagnosis for the subject, the sample level of creatinine of the subject, the estimated glomerular filtration rate of the subject, the sample level of albumin of the subject, and the sample level of blood urea nitrogen of the subject.

The risk factor may be indicative of the risk of suffering CKD for the subject within a prediction time period of three years from the end of the measurement period. The risk factor may be a probability for the subject of developing CKD within three years from the time the sample levels have been determined. Alternatively, the risk factor may be indicative of the risk of suffering CKD for the subject within a time period of less than three years, for example, two years, from the end of the measurement period. As a further alternative, the risk factor may be indicative of the risk of suffering CKD for the subject within a time period of more than three years from the end of the measurement period.

With respect to the computer-implemented method, the determining of the risk factor may comprise the following: providing a machine learning model; providing input data indicative of the plurality of marker parameters to the machine learning model; and determining the risk factor by the machine learning model. Thus, the risk factor is determined by applying the machine learning model trained and tested (validated) before, such training/testing comprising training a machine learning algorithm for creating or determining the machine learning model being the result of such training including training and testing/validating.

The providing of the machine learning model may comprise providing an XGBoost machine learning model. XGBoost provides for a decision-tree-based ensemble machine learning algorithm that uses a gradient boosting framework. Gradient boosting is a machine learning technique for regression and classification problems, which produces a prediction model in the form of an ensemble of weak prediction models, typically decision trees. When a decision tree is the weak learner, the resulting algorithm is called gradient boosted trees, which usually outperforms random forest. It builds the model in a stage-wise fashion like other boosting methods do, and it generalizes them by allowing optimization of an arbitrary differentiable loss function.

The providing of the machine learning model may comprise, in a pre-processing, the following: providing a set of training data for a population of subjects, the training data being indicative of a plurality of training parameters for the population of subjects, wherein the training marker parameters comprising age, level of creatinine, level of estimated glomerular filtration rate, level of albumin, level of blood urea nitrogen, and an indicator whether the subject developed CKD; providing diabetes diagnosis data indicative of a time or date when a diabetes diagnosis was determined for subjects from the population of subjects; determining, from the diabetes diagnosis data, a supplementary training data indicating a time since diagnosis parameter indicative of a time since a diabetes diagnosis was determined for the subjects from the population of subjects; providing an augmented set of training data comprising the set of training data and the supplementary training data; and training the machine learning model such as the XGBoost machine learning model based on the augmented set of training data. The additional parameter referring to the time since diagnosis parameter is determined in a pre-processing, thereby, extending size and number of training data applied for training the machine learning model.

The pre-processing may also comprise a step of determining from the training data a set of preprocessed training data comprising one or more statistical values and/or selected values for one or more of the level of creatinine, estimated glomerular filtration rate, level of albumin, and level of blood urea nitrogen for a respective one or more subjects from the population of subjects. For example, for a subject of the population a plurality of sample levels of creatinine may have been determined. In the preprocessing, one or more statistical values and/or selected values may thus be determined from the plurality of sample levels of creatinine, such as a mean creatinine value and/or a maximum creatinine value for that subject from the population.

A method of training a machine learning model for the determination of a risk factor indicative of the risk of suffering CKD for a test subject from a plurality of marker parameters of the test subject is also provided herein. The method of training comprises:

providing a set of training data for a population of training subjects, the training data being indicative of a plurality of training parameters for the population of training subjects, wherein the training marker parameters comprising at least: age, level of creatinine, level of estimated glomerular filtration rate, level of albumin, and level of blood urea nitrogen, and the training data further comprising for each training subject an indication whether the training subject developed CKD;

optionally determining from the training data a set of preprocessed training data comprising one or more one or more statistical values and/or selected values for one or more of the level of creatinine, estimated glomerular filtration rate, level of albumin, and level of blood urea nitrogen for respective training subjects from the population of training subjects;

providing diabetes diagnosis data indicative of a time or date when a diabetes diagnosis was determined for respective training subjects from the population of training subjects;

determining, from the diabetes diagnosis data, supplementary training data indicating a time since diagnosis parameter indicative of a time since a diabetes diagnosis was determined for the respective training subjects from the population of training subjects;

providing an augmented set of training data comprising the set of training data and/or the set of preprocessed training data and the supplementary training data; and training the machine learning model based on the augmented set of training data for the determination of the risk factor indicative of the risk of suffering CKD for a test subject.

A method for screening a test subject for the risk of chronic kidney disease (CKD) is further provided herein, comprising:

training a machine learning model according to the method of training as described above and thereby obtaining a trained machine learning model;

receiving marker data indicative for a plurality of marker parameters for the test subject, such plurality of marker parameters indicating at least the following: an age value, a time since diagnosis value indicative of a time since a diabetes diagnosis for the subject, a sample level of creatinine, an estimated glomerular filtration rate, a sample level of albumin, and a sample level of blood urea nitrogen; and determining a risk factor indicative of the risk of suffering CKD for the test subject from the plurality of marker parameters by using the trained machine learning model.

The risk factor may be determined using a machine learning model, wherein no marker data are imputed. Thus, machine learning model was trained/tested by training (and testing or validating) data free of imputed marker data.

Within the meaning of the present disclosure, screening a subject for the risk of CKD means identifying a subject at risk of developing or having CKD.

A sample level in the sense of the present disclosure is a level of a substance, such as creatinine or albumin, in a sample of a bodily fluid of the subject. Sample levels may be determined in the same or different samples. Alternatively or additionally, for determining sample levels, measurements may be performed in the same or different samples. For example, a sample level of a substance may be determined from a plurality of measurements of the same substance in the same sample, for example, by determining a mean value. In another example, at least one of a plurality of sample levels of the same substance may be determined in a first sample and at least another one of the plurality of sample levels of the same substance may be determined in a second sample. A sample level of a first substance and a sample level of a second substance may be determined in the same sample. Alternatively, a sample level of a first substance may be determined in a first sample and a sample level of a second substance may be determined in a second sample.

A computer program product may be provided, including a computer readable medium embodying program code executable by a process of a computing device or system, the program code, when executed, causing the computing device or system to perform the computer-implemented method for screening a subject for the risk of chronic kidney disease.

With regard to the computer-implemented method, the alternative embodiments described above may apply mutatis mutandis.

In the computer-implemented method, the program may further cause the processor to execute generating output data indicative of the risk factor and outputting the output data to an output device of the data processing system. The output device may be any device suitable for outputting the output data, for example, a display device of the data processing system, such as a monitor, and/or a transmitter device for transmitting for wired and/or wireless data transmission. The output data may be output to a user, for example, a physician, via a display of the data processing system. Based on the output data indicative of the risk factor, further marker data may be requested from the subject and/or a future date for a further screening of the subject for CKD may be set (e.g., then based on at least one or more newly collected sample levels of one or more of creatinine, albumin, blood urea nitrogen and/or a newly determined estimated glomerular filtration rate, new age value, new time since diagnosis value indicative of the time since the diabetes diagnosis for the subject considering the future date).

The data processing system may comprise a plurality of data processing devices, each data processing device having a processor and a memory. The marker data may be provided in a first data processing device. For example, the marker data may be received in the first data processing device by user input via an input device and/or by data transfer. The marker data may be sent from the first data processing device to a second data processing device which may be located remotely with respect to the first data processing device. The marker data may be received in the second data processing device and the risk factor may then be determined in the second data processing device. Result data indicative of the risk factor may be sent from the second data processing device to the first data processing device or, alternatively or additionally, to a third data processing device. The result data may then be stored in the first and/or the third data processing device and/or output via an output device of the first and/or the third data processing device.

The first data processing device and/or the third data processing device may be a local device, such as a client computer, and the second data processing device may be a remote device, such as a remote server.

Alternatively, the functionality of at least the first data processing device and the second data processing device may be provided in the same data processing device, for example, a computer, such as a computer in a physician's office. All steps of the computer-implemented method may be executed in the same data-processing device.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
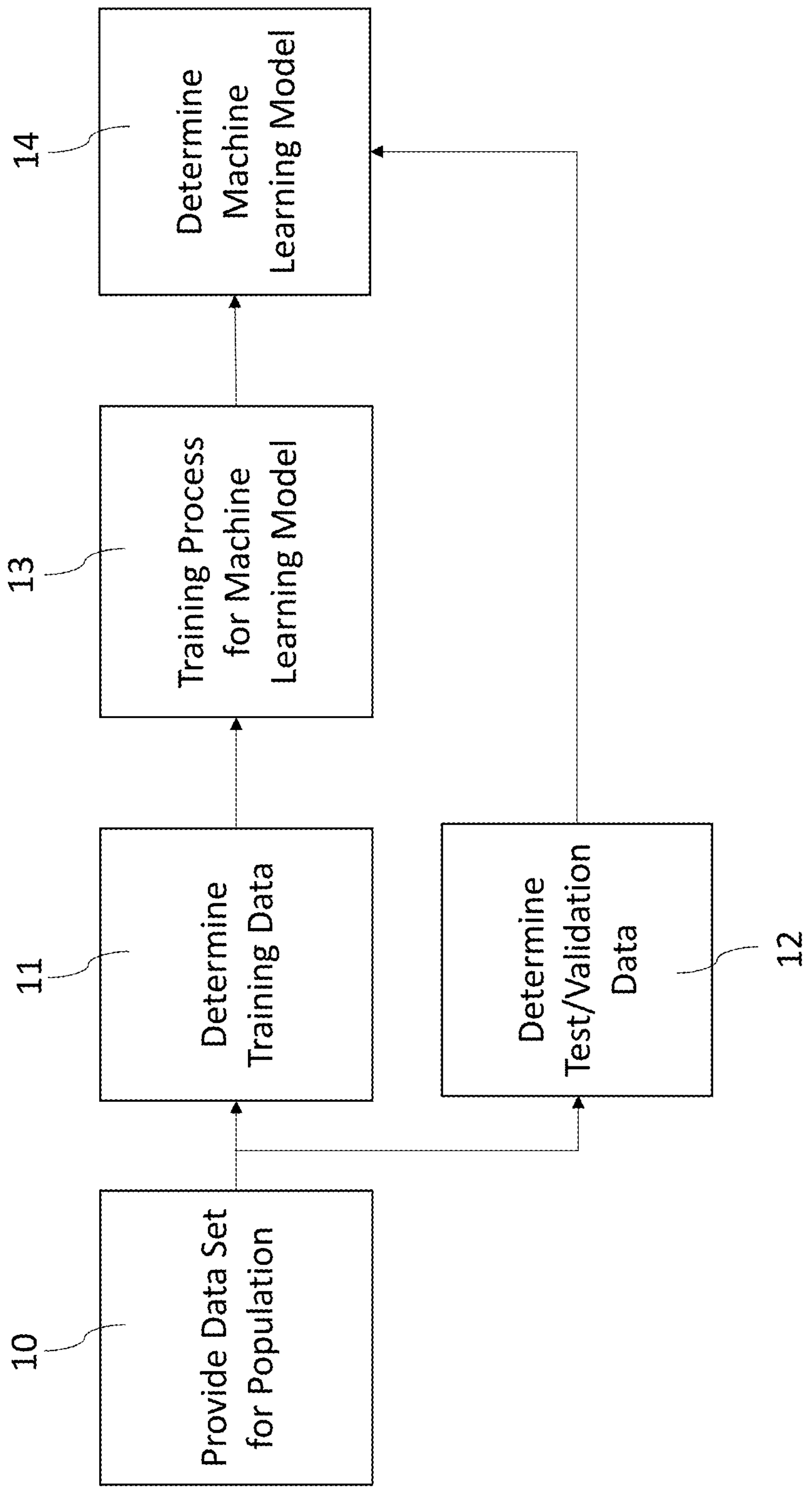
FIG. 1 is a schematic representation for determining an XGBoost machine learning model.

FIG. 1 shows a schematic representation for determining or creating—by training and testing/validating a machine learning algorithm—a machine learning model, the machine learning model implemented, in an example, with a an XGBoost machine learning model. A data set for a population of subjects is provided in step 10.

A machine learning model is created using electronic health record (EHR) data, for example, from several hundred thousands of people with diabetes (type 1 or type 2) represented in a database. The data is retrieved for the time window after the initial diagnosis of diabetes. The data can be considered as real-world data (RWD) and no general restrictions on, for example, completeness or veracity of the data are applied.

No missing data are imputed for teaching or learning (training and testing/validating) the model. An XGBoost machine learning process has been applied.

In an example the data set was provided from the so-called IBM Explorys database (see Kaelber, D. C. et al., *Patient characteristics associated with venous thromboembolic events: a cohort study using pooled electronic health*

*record data*, J Am Med Inform Assoc 19, 965-972, 2012). An alternative example for a data set for a population of subjects is the Indiana Network for Patient Care (INPC) database (see McDonald, C. J. et al., *The Indiana Network for Patient Care: a working local health information infrastructure*, Health Affairs 24, 1214-1220, 2005).

The database provides indication as to a date of diabetes diagnosis for the subjects. Starting from such information a new parameter is established such parameter providing indication of a time period since diabetes diagnosis for the respective subject. A pre-processing step is applied for determining such additional parameter from the diabetes diagnosis data provided in the database. It provides for a supplementary training data indicating a time since diagnosis parameter indicative of the time since a diabetes diagnosis was determined for the subjects from the population of subjects. Thus, there is an augmented set of training data comprising in addition the supplementary training data.

From the data set including supplementary training data indicating the time since diagnosis parameter, a set of training data and a set of test/validation data are determined (steps 11, 12). The set of training data is indicative of a plurality of parameters for the population of subjects (step 11). With regard to the data set provided for the population of subjects, the set of training data may comprise training data indicative of (almost) all parameters for which data are provided in the data set of the population of subjects. Alternatively, a subset of parameters may be selected for training of the machine learning model.

Following, there is a training process for a machine learning model in step 13 based on the set of training data. In an example, in the training process a XBoost training is applied for determining or creating a XBoost machine learning model. The machine learning model is finally determined in step 14 applying the set of test/validation data for final model evaluation.

Figure 2:
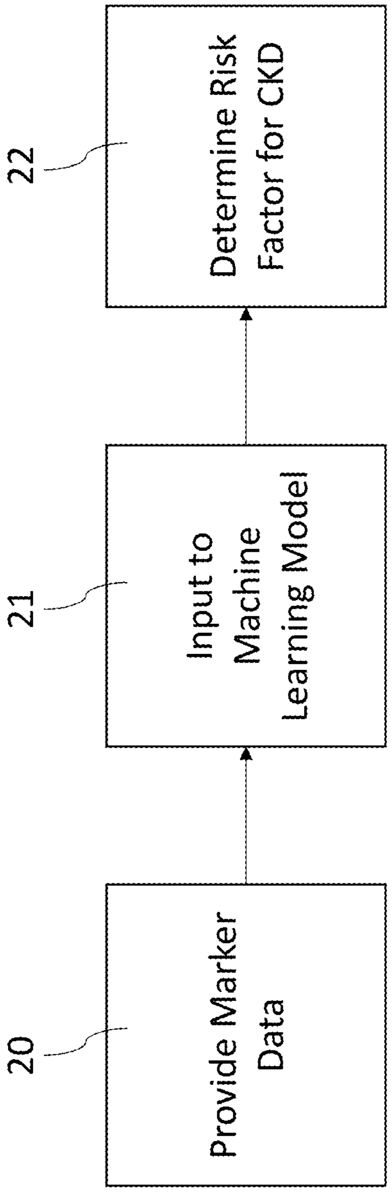
FIG. 2 is a schematic representation for a computer-implemented method for determining a risk factor indicative of a risk of CKD for a subject.

FIG. 2 shows a schematic representation with respect to a computer-implemented method for determining a risk factor indicative of a risk of chronic kidney decease (CKD) for a subject. In step 20 marker data are provided which are indicative of a plurality of marker parameters for the subject for which the risk factor is to be determined. In an example, the plurality of marker parameters is indicative of: an age value, a time since diagnoses value indicative of a time since a diabetes diagnoses for the subject, a sample level of creatinine, an estimated glomerular filtration rate (eGFR), a sample level of albumin, and a sample level of blood urea nitrogen (BUN). The marker data are provided as an input to the machine learning model (step 21). By applying the machine learning model a risk factor for the risk of chronic kidney decease for the subject is determined (step 22). The machine learning model is implemented by a software application on a data processing device having a processor and a memory.

In general, in any of the embodiments of the method for screening a subject for the risk of CKD, $\text{creatinine}_{max}$ may be a maximum sample level of creatinine from a plurality of sample levels of creatinine for the subject, $\text{albumin}_{min}$ may be a minimum sample level of albumin from a plurality of sample levels of albumin for the subject, $\text{eGFR}_{min}$ may be a minimum estimated glomerular filtration rate from a plurality of estimated glomerular filtration rates for the subject, $\text{BUN}_{min}$ may be a minimum blood sample level of urea nitrogen. Such values and/or sample levels may be determined from values and/or sample levels already on file for the subject. Alternatively or in addition, values and/or sample levels may be determined for the subject specifically for use with the method for screening a subject for the risk of CKD. Values and/or sample levels may be real world data, i.e., unlike clinical data, they may not be restricted regarding, for example, completeness or veracity of the data.

ICD codes may be used as target variables for training as well as the CKD reference diagnosis in the analysis of the validation results. The definition of the target feature "CKD" may be solely based on the occurrence of the respective ICD codes in the databases. In order to maintain the RWD character of the data set, no additions or changes may be made to the databases. Such ICD codes may comprise ICD-9 codes and ICD-10 codes, for example, the following ICD codes: 250.40, 250.41, 250.42, 250.43, 585.1, 585.2, 585.3, 585.4, 585.5, 585.6, 585.9, 403.00, 403.01, 403.11, 403.90, 403.91, 404.0, 404.00, 404.01, 404.02, 404.03, 404.1, 404.10, 404.11, 404.12, 404.13, 404.9, 404.90, 404.91, 404.92, 404.93, 581.81, 581.9, 583.89, 588.9, E10.2, E10.21, E10.22, E10.29, E11.2, E11.21, E11.22, E11.29, N17.0, N17.1, N17.2, N17.8, N17.9, N18.1, N18.2, N18.3, N18.4, N18.5, N18.6, N18.9, N19, 112.0, 112.9, 113, 113.0, 113.1, 113.10, 113.11, 113.2, N04.9, N05.8, N08 and/or N25.9.

In an embodiment, the ICD-9 codes 250.40, 403.90, 585.3, 585.9 are the most abundant diagnosis in the respective time windows of the data.

ICD codes may also be used to determine a diabetes diagnosis. E.g., type 1 diabetes diagnosis may be based on ICD-9 codes 250._1 and/or 250._3, and/or ICD-10 codes E10.%. E.g., type 2 diabetes diagnosis may be based on ICD-9 codes 250._0 and/or 250._2, and/or ICD-10 codes E11.%. "_" and "%" are placeholders, wherein "_" may not be empty; However, the placeholder "%" may be empty.

Experimental Data

The area under the receiver operating characteristic (ROC) (compare Swets, J. A., *Measuring the accuracy of diagnostic systems*, Science 240, 1285-1293, 1988) curve (AUC) is frequently used to measure the quality of clinical markers as well as machine learning algorithms/models (see Bradley, A. P., *The use of the area under the ROC curve in the evaluation of machine learning algorithms*, Pattern Recognition 30, 1145-1159, 1997). A perfect marker would achieve AUC=1.0, whereas flipping a coin would result in AUC=0.5.

Machine learning models applying XGBoost in the learning procedure have been trained and tested based on different sets of training data referring to all parameters available in the database or a subset of the parameters. A machine learning model referred to as "Full XG boost model" has been trained using all parameters from the plurality of parameters such as about 100 (about 948 features) available in the IBM Explorys database. Parameters in this context refers to, e.g., creatinine, albumin, age etc. Features in this context, e.g., refers to selected or statistical values, such $\text{creatinine}_{max}$ or $\text{creatinine}_{medium}$. The "Full XG boost model" was created by using all available parameters (all features). With respect to the data from the database, not all parameters are available for every patient (subject) of the population. When working with the full set of parameters it was found that certain parameters are particularly important (e.g. top 5 or top 20 or top 30).

Further, a machine learning model referred to as "Top 20 XG boost model" has been created (training and testing) using only a subset of the data from the IBM Explorys database. In an embodiment, the data of the subset of data are relating to (only) 20 parameters from the plurality of parameters, the 20 parameters being parameters which were found most important in the machine learning process for the "Full XG boost model." Following, such 20 parameters are listed (not in an order of importance): age; albumin (serum and/or plasma); albumin (urine), systolic blood pressure, blood urea nitrogen (BUN), medication with antihypertensive drugs, medication with insulin; number of pre-existing conditions of: diabetic retinopathy, ischemic heart disease, peripheral artery occlusive disease, cerebrovascular disease; creatinine (serum/plasma); time (days) since diabetes diagnosis; mean time span between two doctor's visits where a parameter has been measured or a diagnosis has been made; diagnosis with DM type 2 with hyperglycemia; diagnosis of heart failure; estimated glomerular filtration rate (eGFR); erythrocytes (serum and/or plasma); glucose (serum and/or plasma); hematocrit; hemoglobin; urine albumin-to-creatinine ratio (UACR); and body weight.

In the training (learning procedure) of the "Top 20 XG boost model" created as a separate model, only the top 20 parameters determined from the training of the "Full XGBoost model" were used. Thus, other parameters (even though possibly available) were ignored when the "Top 20 XG boost model" was determined.

For evaluating the machine learning models for both the "Full XG boost model" and the "Top 20 XG boost model" AUC was determined for population of subjects for which the database provides real world data. Such calculation was performed for the population of subjects taking into account all parameters (features) available. In addition, the calculation was performed for the population of subjects taking into account only data related to the following (six) parameters: age, time since diabetes, creatinine, estimated glomerular filtration rate (eGFR), albumin, and blood urea nitrogen (BUN) ("using limited number of parameters").

For comparison, AUC was calculated for a logistic regression (LR) model also trained based on the data of the subset of data relating to the 20 parameters from the plurality of parameters. Such machine learning model is referred to as "LR Top 20 model." For the "LR Top 20 model (only limited number of parameters)," the AUC calculation and specificity @ 90% Sensitivity were assessed by considering only the subject specific data relating to the following (six) parameters: age, time since diabetes, creatinine, estimated glomerular filtration rate (eGFR), albumin, and blood urea nitrogen (BUN) ("using limited number of parameters"). For the 14 other parameters, no subject specific data were used, but for those other parameters data were imputed from cohorts selected or statistical values, respectively.

The performance of a method for screening a subject for the risk of CKD or for identifying those people at high risk of developing CKD may be judged according to sensitivity (fraction of correctly predicted high-risk patients) and specificity (fraction of correctly assigned low-risk patients). However, either of these numbers can be improved at the expense of the other simply by changing the threshold between high and low risk. Hence, data pairs of sensitivity and specificity may be illustrated in forms of the so-called receiver operating characteristic (ROC) curve (see Swets, J. A., *Measuring the accuracy of diagnostic systems*, Science 240, 1285-1293, 1988) in which the sensitivity is plotted as a function of 1-specificity (which corresponds to the fraction of falsely assigned high-risk persons).

Results of the calculations conducted for all parameters or only the six parameters identified above for the data from the Indiana Network for Patient Care (INPC) database are shown in Table 1.

TABLE 1

| | AUC | Specificity @ 90% Sensitivity |
|---|---|---|
| "Full XGBoost model" (using all features) | 0.849 | 0.555 |
| "Top20 XGBoost model" (using all features) | 0.842 | 0.537 |
| "Full XGBoost Model" (using only limited number of parameters) | 0.828 | 0.499 |
| "Top20 XGBoost Model" (using only limited number of parameters) | 0.823 | 0.484 |
| "LR Top 20 model" (using all features) | 0.819 | 0.470 |
| "LR Top 20 Model" (only limited number of parameters) | 0.809 | 0.441 |

As can be seen from Table 1, AUC for the machine learning models are high for all depicted models, but by applying XGBoost even better results could be achieved than for the LR model. Using only the limited number of parameters for calculating AUC still provides reliable result.

Figure 3:
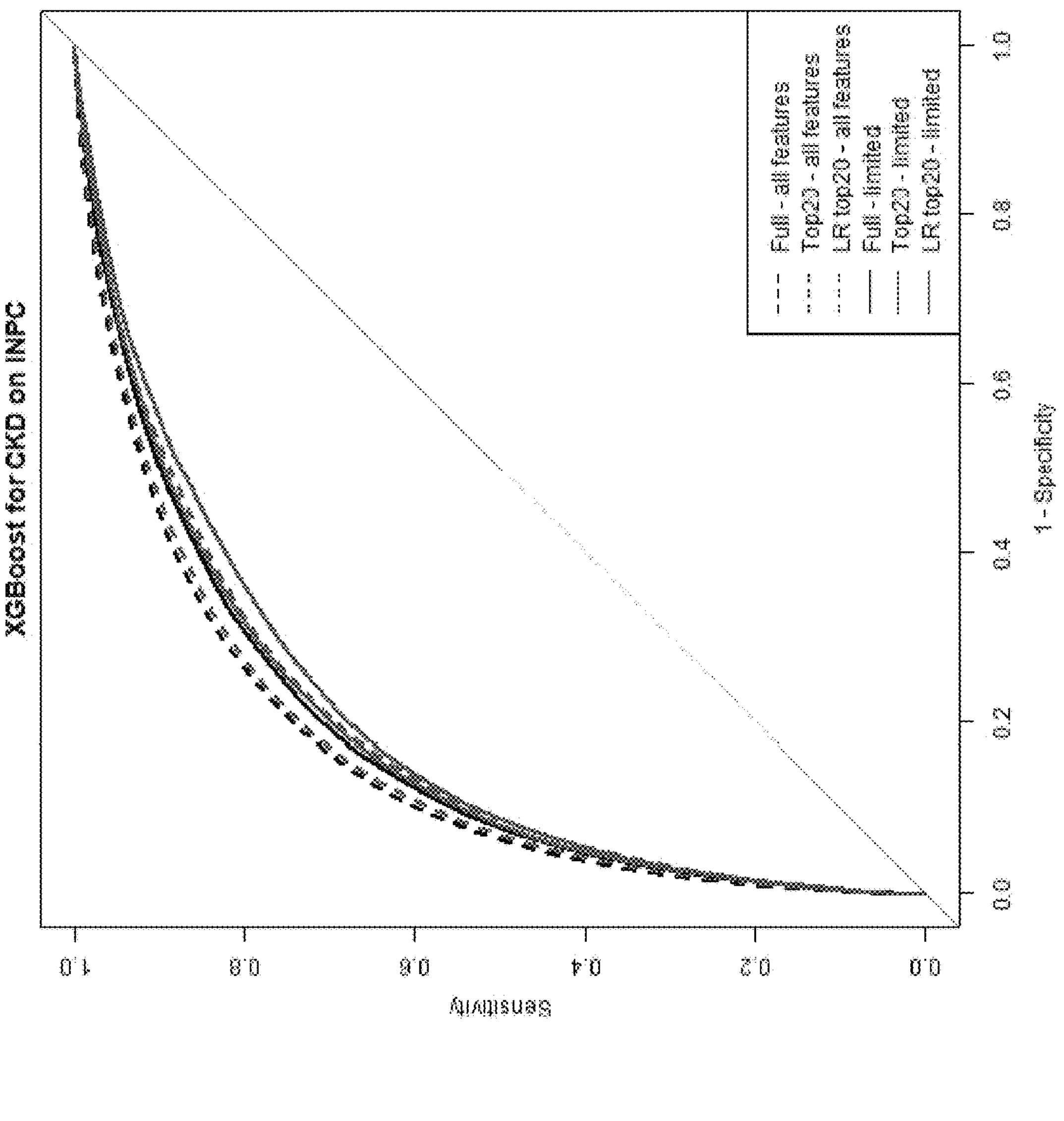
FIG. 3 is an ROC curve for the "Full XG boost model," the "Top 20 XG boost model," and the "LR Top 20 model" for both using all parameters and using only limited number of parameters.

FIG. 3 shows the ROC curve for the "Full XG boost model," the "Top 20 XG boost model," and the "LR Top 20 model" for both using all parameters and using only limited number of parameters. For a perfect classifier, the ROC curve reaches the upper-left corner. In fact, the threshold corresponding to the data pair closest to this corner is dubbed the "optimal threshold." When aiming for high sensitivity, an alternative threshold may be chosen to guarantee a sensitivity of, for example, 90%.

For additionally comparing the machine leaned XGBoost model presented here, calculations were also conducted for a model (algorithm) for predicting a risk factor for CKD known from EP 3 543 702 A1, the model referred to as "Algorithm model" in the following. The "Algorithm model" also applies logistic regression. No data imputation was applied. Results of the calculations conducted for data from the IBM Explorys database are shown in Table 2.

TABLE 2

| | AUC | Specificity @ 90% Sensitivity |
|---|---|---|
| "Full XGBoost model" (using all features) | 0.836 | 0.519 |
| "Top20 XGBoost model" (using all features) | 0.829 | 0.499 |
| "Algorithm model" | 0.769 | 0.347 |

From Table 2 it is concluded that the machine learning model applying XGBoost provides improved results in terms of risk factor determination over the "Algorithm model."

In summary, it is demonstrated that different machine learning models for predicting a risk factor for CKD performed robust even if only a limited number of marker parameters is available (specific selection of marker parameters): age, time since diabetes, creatinine, estimated glomerular filtration rate (eGFR), albumin, and blood urea nitrogen (BUN). The results support the path towards high-quality predictive models that can be applied in a clinical setting, enabling the shift towards personalized and outcome-based healthcare.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A method for screening a subject for the risk of chronic kidney disease (CKD), the method comprising:
- receiving marker data indicative for a plurality of marker parameters for a subject, the plurality of marker parameters indicating at least the following:
  - an age value,
  - a time since diagnosis value indicative of a time since a diabetes diagnosis for the subject,
  - a sample level of creatinine,
  - an estimated glomerular filtration rate,
  - a sample level of albumin, and
  - a sample level of blood urea nitrogen; and
- determining a risk factor indicative of the risk of suffering CKD for the subject from the plurality of marker parameters, wherein determining of the risk factor comprises
  - providing a machine learning model;
  - providing input data indicative of the plurality of marker parameters to the machine learning model; and
  - determining the risk factor by the machine learning model.

2. The method of claim 1, wherein the plurality of marker parameters indicates, for the subject, a blood sample level of creatinine.

3. The method of claim 1, wherein the plurality of marker parameters indicates, for the subject, at least one of a blood sample level of albumin and a urine sample level of albumin.

4. The method of claim 1, wherein the step of receiving marker data comprises receiving marker data indicative for a plurality of marker parameters for the subject for a measurement period of two years or less.

5. The method of claim 1, wherein the age value corresponds to the age of the subject when determining the risk factor.

6. The method of claim 1, wherein the time since diagnosis value is indicative of the time since the diabetes diagnosis for the subject when determining the risk factor.

7. The method of claim 1, wherein the risk factor is indicative of the risk of suffering CKD for the subject within a prediction time period of three years.

8. A computer-implemented method for screening a subject for the risk of chronic kidney disease (CKD) in a data processing system having a processor and a non-transitory memory storing a program causing the processor to execute:
- a) receiving marker data indicative for a plurality of marker parameters for a subject, such plurality of marker parameters indicating at least
  - an age value,
  - a value indicating a time since a diabetes diagnosis for the subject,
  - a sample level of creatinine,
  - an estimated glomerular filtration rate,
  - a sample level of albumin, and
  - a sample level of blood urea nitrogen; and
- b) determining a risk factor indicative of the risk of suffering CKD for the subject from the plurality of marker parameters, wherein determining of the risk factor comprises
  - providing a machine learning model;
  - providing input data indicative of the plurality of marker parameters to the machine learning model; and
  - determining the risk factor by the machine learning model.

9. The computer-implemented method of claim 8, wherein the machine learning model comprises providing an XGBoost machine learning model.

10. The computer-implemented method of claim 8, wherein the providing of the machine learning model comprises:
- providing a set of training data for a population of subjects, the training data being indicative of a plurality of training parameters for the population of subjects, wherein the training parameters comprise: age, level of creatinine, estimated glomerular filtration rate, level of albumin, level of blood urea nitrogen, and an indicator whether the subject developed CKD;
- providing diabetes diagnosis data indicative of a time or date when a diabetes diagnosis was determined for subjects from the population of subjects;
- determining, from the diabetes diagnosis data, a supplementary training data indicating a time since diagnosis parameter indicative of a time since a diabetes diagnosis was determined for the subjects from the population of subjects;
- providing an augmented set of training data comprising the set of training data and the supplementary training data; and
- training the machine learning model based on the augmented set of training data.

11. The computer-implemented method of claim 8, wherein the risk factor is determined using the machine learning model with no marker data imputed.

12. A system comprising a processor and a non-transitory memory storing a program causing the processor to perform the method of claim 8 for screening a subject for the risk of chronic kidney disease (CKD).

13. A non-transitory computer readable medium having stored thereon computer-executable instructions for performing the method according to claim 8.

* * * * *